(12) United States Patent
Giladi et al.

(10) Patent No.: US 11,879,886 B2
(45) Date of Patent: Jan. 23, 2024

(54) SYSTEM FOR VIEWING CELL CULTURES UNDER A MICROSCOPE WHILST APPLYING

(71) Applicant: Novocure GmbH, Root (CH)

(72) Inventors: Moshe Giladi, Haifa (IL); Yoram Wasserman, Haifa (IL); Yoram Palti, Haifa (IL); Michael Krinitsky, Beer Sheva (IL); Michael Shtotland, Haifa (IL)

(73) Assignee: Novocure GmbH, Root (CH)

( * ) Notice: Subject to any disclaimer, the term of this patent is extended or adjusted under 35 U.S.C. 154(b) by 0 days.

(21) Appl. No.: 18/092,742

(22) Filed: Jan. 3, 2023

(65) Prior Publication Data

US 2023/0141087 A1 May 11, 2023

Related U.S. Application Data

(62) Division of application No. 15/872,318, filed on Jan. 16, 2018, now Pat. No. 11,573,221.

(Continued)

(51) Int. Cl.
*G01N 33/483* (2006.01)
*G01N 15/14* (2006.01)
(Continued)

(52) U.S. Cl.
CPC ....... *G01N 33/4836* (2013.01); *G01N 33/574* (2013.01); *G02B 21/34* (2013.01); *G02B 21/0088* (2013.01)

(58) Field of Classification Search
CPC .......................... G01N 33/4836; G01N 33/574
(Continued)

(56) References Cited

U.S. PATENT DOCUMENTS

| 6,868,289 B2 | 3/2005 | Palti |
| 7,016,725 B2 | 3/2006 | Palti |

(Continued)

FOREIGN PATENT DOCUMENTS

| EP | 2682478 A1 | 1/2014 |
| EP | 3095853 A1 | 11/2016 |

OTHER PUBLICATIONS

Giladi et al., "Microbial Growth Inhibition by Alternating Electric Fields", Antimicrobial Agents and Chemotherapy, vol. 52, Oct. 2008, p. 3517-3522.

(Continued)

*Primary Examiner* — Lydia Edwards
(74) *Attorney, Agent, or Firm* — Potomac Law Group, PLLC

(57) ABSTRACT

An apparatus includes a bottom panel with a transparent region and ceramic sidewalls affixed to the bottom panel to form a container. Electrodes are disposed on the outer surface of the sidewalls at positions selected so that when a sample is positioned in the container, applying a voltage between the electrodes induces an electric field through the sample. Electrical conductors provide contact with the electrodes. All the components are sized and shaped to facilitate positioning of the container on the stage of an inverted microscope so that when the sample is positioned in the container, light emanating from a light source is free to travel along an optical path that passes through the sample, through the transparent region, and into the objective of the inverted microscope. The electrodes and conductors are positioned with respect to the transparent region so as not to interfere with the optical path.

8 Claims, 3 Drawing Sheets

Related U.S. Application Data

(60) Provisional application No. 62/448,152, filed on Jan. 19, 2017.

(51) Int. Cl.
  *F21V 8/00* (2006.01)
  *G01N 33/574* (2006.01)
  *G02B 21/34* (2006.01)
  *G02B 21/00* (2006.01)

(58) Field of Classification Search
  USPC ..................................................... 435/288.7
  See application file for complete search history.

(56) References Cited

U.S. PATENT DOCUMENTS

| | | |
|---|---|---|
| 7,089,054 B2 | 8/2006 | Palti |
| 7,136,699 B2 | 11/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 2006/0167499 A1 | 7/2006 | Palti |
| 2007/0225766 A1 | 9/2007 | Palti |
| 2007/0239213 A1 | 10/2007 | Palti |
| 2009/0076366 A1 | 3/2009 | Palti |
| 2012/0283726 A1 | 11/2012 | Palti |
| 2014/0330268 A1 | 11/2014 | Palti et al. |
| 2015/0344161 A1 | 12/2015 | Selker et al. |
| 2016/0326480 A1 | 11/2016 | Saito et al. |
| 2017/0120041 A1 | 5/2017 | Wenger et al. |
| 2017/0215939 A1 | 8/2017 | Palti et al. |
| 2017/0281934 A1 | 10/2017 | Gliadi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |
| 2021/0060334 A1 | 3/2021 | Avraham et al. |
| 2021/0069503 A1 | 3/2021 | Tran et al. |

OTHER PUBLICATIONS

Giladi et al., "Mitotic Spindle Disruption by Alternating Electric Fields Leads to Improper Chromosome Segregation and Mitotic Catastrophe in Cancer Cells," Scientific Reports, vol. 5, No. 1, pp. 1-16, Dec. 2015.

International Preliminary Report on patentability dated May 10, 2019, issued in international application No. PCT/IB2018/050265.

International Search Report and Written Opinion issued in application No. PCT/IB2018/050265 dated Mar. 29, 2018.

Novocure Limited, "Novocure Announces Launch of the inovitro Laboratory Research System," press release dated Nov. 21, 2013.

Written Opinion of the International Searching Authority issued in application No. PCT/IB2018/050265, dated Jan. 29, 2019.

SYSTEM FOR VIEWING CELL CULTURES UNDER A MICROSCOPE WHILST APPLYING

CROSS REFERENCE TO RELATED APPLICATIONS

This Application is a divisional of U.S. application Ser. No. 15/872,318, filed Jan. 16, 2018, which claims the benefit of U.S. Provisional Application 62/448,152, filed Jan. 19, 2017, each of which is incorporated herein by reference in its entirety.

BACKGROUND

Tumor Treating Fields (TTFields) are low intensity electric fields in the intermediate frequency range that target solid tumors by disrupting mitosis. When treating patients, TTFields are delivered via transducer arrays made from a plurality of ceramic disks with a high dielectric constant (as described, for example, in U.S. Pat. No. 8,715,203, which is incorporated herein by reference). The transducer arrays capacitively couple the electric field into the patient's body.

The Inovitro™ system supplied by Novocure is an existing system for studying TTFields in vitro. The Inovitro™ system includes ceramic culture dishes constructed to capacitively couple electric field into the cell culture while the cell cultures are maintained at a controlled temperature. This is used to simulate the capacitive coupling of the electric fields into a patient's body.

SUMMARY OF THE INVENTION

One aspect of the invention is directed to a first apparatus for applying electric fields to a sample and for observing the sample using an inverted microscope while the sample is illuminated by a light source. The inverted microscope has a stage and an objective. This first apparatus comprises a bottom panel, ceramic sidewalls, a plurality of electrodes, and a plurality of electrical conductors. The bottom panel has a transparent region. The ceramic sidewalls are affixed to the bottom panel such that the ceramic sidewalls and the bottom panel cooperate to form a container for holding the sample, wherein the ceramic sidewalls are affixed to the bottom panel at a position that surrounds the transparent region, and wherein the ceramic sidewalls have at least one outer surface. The plurality of electrodes are disposed on the at least one outer surface of the ceramic sidewalls at positions selected so that when the sample is positioned in the container, application of a voltage between the plurality of electrodes induces an electric field through the sample. Each of the plurality of electrical conductors provides electrical contact with a respective one of the plurality of electrodes. The bottom panel, the transparent region, and the ceramic sidewalls are sized and shaped to facilitate positioning of the container on the stage of the inverted microscope so that when the sample is positioned in the container, light emanating from the light source is free to travel along an optical path that passes through the sample, through the transparent region, and into the objective of the inverted microscope. And each of the plurality of electrodes and each of the plurality of electrical conductors is positioned with respect to the transparent region so as not to interfere with the optical path.

In some embodiments of the first apparatus, the ceramic sidewalls are cylindrical.

Some embodiments of the first apparatus further comprise at least one thermistor mounted to the ceramic sidewalls at a position that does not interfere with the optical path. Some embodiments of the first apparatus further comprise at least one thermistor mounted to the bottom panel at a position that does not interfere with the optical path.

In some embodiments of the first apparatus, the ceramic sidewalls are mounted to the bottom panel using an adhesive.

In some embodiments of the first apparatus, the ceramic sidewalls are mounted to the bottom panel using a screw mount configured to squeeze the ceramic sidewalls and the bottom panel together. Some of these embodiments further comprise an O-ring disposed between the ceramic sidewalls and the bottom panel.

In some embodiments of the first apparatus, the ceramic sidewalls are mounted to the bottom panel using an O-ring that has (a) an outer diameter that matches the inner diameter of a Petri dish and (b) an inner diameter that matches the outer diameter of the cylindrical sidewalls, and the cylindrical sidewalls are jammed into the O-ring to provide an interference fit.

In some embodiments of the first apparatus, the entire bottom panel is transparent.

Some embodiments of the first apparatus further comprise at least one thermistor mounted to the container at a position that does not interfere with the optical path. In these embodiments, the entire bottom panel is transparent, the ceramic sidewalls are cylindrical, and the second direction is roughly perpendicular to the first direction.

In some embodiments of the first apparatus, the plurality of electrodes comprises at least four electrodes disposed on the at least one outer surface of the ceramic sidewalls at positions selected so that when the sample is positioned in the container, (a) application of a voltage between a first subset of the at least four electrodes induces an electric field in a first direction through the sample, and (b) application of a voltage between a second subset of the at least four electrodes induces an electric field in a second direction through the sample. The plurality of electrical conductors comprises at least four electrical conductors, and each of the at least four electrical conductors provides electrical contact with a respective one of the at least four electrodes. In some of these embodiments, the second direction is roughly perpendicular to the first direction.

Another aspect of the invention is directed to a second apparatus for optically observing a sample while applying electric fields to the sample. This second apparatus comprises a fluid tight container; first, second, third, and fourth electrodes; and first, second, third, and fourth electrical conductors. The fluid-tight container is shaped and dimensioned for holding the sample, and the container has a transparent bottom panel and ceramic sidewalls affixed to the transparent bottom panel, wherein the ceramic sidewalls have at least one outer surface. The first electrode is disposed at a first position on the at least one outer surface of the ceramic sidewalls. The second electrode is disposed at a second position on the at least one outer surface of the ceramic sidewalls, wherein the second position is opposite to the first position, so that application of an AC voltage between the first electrode and the second electrode induces an AC electric field through the sample in a first direction. The third electrode is disposed at a third position on the at least one outer surface of the ceramic sidewalls. The fourth electrode is disposed at a fourth position on the at least one outer surface of the ceramic sidewalls, wherein the fourth position is opposite to the third position, so that application of an AC voltage between the third electrode and the fourth electrode induces an AC electric field through the sample in a second direction. The first electrical conductor is arranged to route electricity between a first electrical terminal and the first electrode along a path that circumvents the transparent bottom panel. The second electrical conductor is arranged to route electricity between a second electrical terminal and the second electrode along a path that circumvents the transparent bottom panel. The third electrical conductor is arranged to route electricity between a third electrical terminal and the third electrode along a path that circumvents the transparent bottom panel. And the fourth electrical conductor is arranged to route electricity between a fourth electrical terminal and the fourth electrode along a path that circumvents the transparent bottom panel.

In some embodiments of the second apparatus, the first electrical terminal, the second electrical terminal, the third electrical terminal, and the fourth electrical terminal are all disposed in a single electrical connector. In some embodiments of the second apparatus, the ceramic sidewalls are cylindrical.

Some embodiments of the second apparatus further comprise at least one thermistor mounted to the ceramic sidewalls.

In some embodiments of the second apparatus, the ceramic sidewalls are mounted to the bottom panel using an adhesive. In some of these embodiments, the container has an O-ring disposed between the ceramic sidewalls and the bottom panel, and the ceramic sidewalls are mounted to the bottom panel using a screw mount configured to squeeze the ceramic sidewalls and the bottom panel together.

In some embodiments of the second apparatus, the ceramic sidewalls are mounted to the bottom panel using an O-ring that has (a) an outer diameter that matches the inner diameter of a Petri dish and (b) an inner diameter that matches the outer diameter of the cylindrical sidewalls, and the cylindrical sidewalls are jammed into the O-ring to provide an interference fit.

In some embodiments of the second apparatus, the second direction is roughly perpendicular to the first direction.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
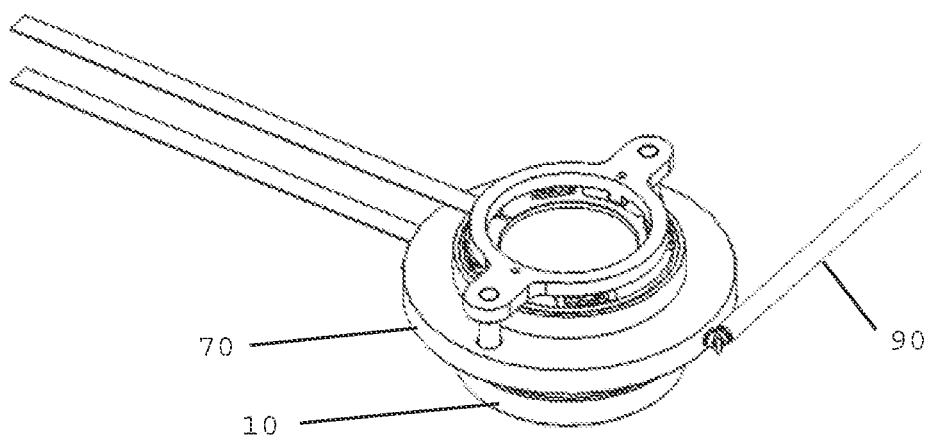
FIG. 1 is an assembled view of a first embodiment of an apparatus for viewing cell cultures under a microscope whilst applying TTFields.

One limitation of the Inovitro™ system is that the construction of the ceramic culture dishes and the circuitry for applying electrical signals to the electrodes on the dishes makes it impossible to perform live-cell microscopy experiments on cells while those cells are being subjected to TTFields. The embodiments described below overcome this disadvantage.

FIGS. 1-5 depict various views of an embodiment of a dish-like apparatus for applying electric fields to a sample and for observing the sample using an inverted microscope while the sample is illuminated by a light source. This embodiment facilitates time lapse microscopy during the application of TTFields. The inverted microscope that is used to observe the sample will typically have a stage and an objective. The dish-like apparatus may be designed to sit directly on the stage of the inverted microscope while the inverted microscope is positioned in an incubator (which optionally may provide any necessary gases to the sample).

To allow light to flow through the sample for the purpose of microscopy experiments or other imaging techniques, the dish-like apparatus has a bottom panel 20 with a transparent region. In the illustrated embodiment, the entire bottom panel 20 is transparent. However, in alternative embodiments, only a portion of the bottom panel 20 may be transparent. In the illustrated embodiment, the floor of a glass Petri dish 10 serves as the bottom panel 20. Preferably, the transparent region does not introduce optical distortions. In those embodiments that use the floor of a glass Petri dish to serve as the bottom panel, Ibidi® dishes may be used to minimize optical distortions.

Ceramic sidewalls 30 (visible in FIGS. 3-5) are affixed to the bottom panel 20 such that the ceramic sidewalls 30 and the bottom panel 20 cooperate to form a container that is shaped and dimensioned for holding the sample. In those embodiments where only a portion of the bottom panel 20 is transparent, the ceramic sidewalls 30 are affixed to the bottom panel 20 at a position that surrounds the transparent region. In those embodiments where the entire bottom panel 20 is transparent, the ceramic sidewalls 30 may be affixed to the bottom panel 20 anywhere (e.g. close to the perimeter of the bottom panel). In this case, a portion of the bottom panel 20 that lies within the boundaries of the ceramic sidewalls 30 will serve as the transparent region. The ceramic sidewalls 30 are preferably made from a of a high capacitance material (e.g. PMN-PT).

The bottom panel 20, the transparent region of the bottom panel 20, and the ceramic sidewalls 30 are sized and shaped to facilitate positioning of the container on the stage of the inverted microscope so that when the sample is positioned in the container, light emanating from the light source is free to travel along an optical path that passes through the sample, through the transparent region of the bottom panel 20, and into the objective of the inverted microscope.

In some preferred embodiments (including the illustrated embodiment), the ceramic sidewalls 30 are formed from a single cylindrical tube. In these embodiments, the ceramic sidewalls 30 will have a single cylindrical outer surface. In alternative embodiments, ceramic sidewalls 30 with different shapes may be used (e.g. square or octagonal). In these embodiments, the ceramic sidewalls 30 will have two or more outer surfaces. For example, in those embodiments where the square ceramic sidewalls are used, the ceramic sidewalls will have four outer surfaces.

In some embodiments, the ceramic sidewalls 30 are mounted to the bottom panel 20 using an adhesive (e.g., biocompatible glue or cement).

In alternative embodiments, the ceramic sidewalls 30 are mounted to the bottom panel 20 using a screw mount configured to squeeze the ceramic sidewalls 30 and the bottom panel 20 together. For example, the upper housing 70 can connect to a Petri dish 10 using a threaded screw-mount connection which includes a set of external threads (not shown) on the upper housing 70 and a corresponding set of internal threads (not shown) on the Petri dish 10. In these embodiments, an O-ring 75 is preferably positioned between the ceramic sidewalls 30 and the bottom panel 20 of the Petri dish 10 such that the O-ring 75 is compressed when the upper housing 70 is screwed into the Petri dish 10. The O-ring 75 seals liquids into the volume defined by the bottom panel 20 and the cylindrical sidewalls 30. The upper housing 70 has an opening 72 through which samples can be inserted into the Petri dish 10.

In alternative embodiments, instead of using a screw mount, an O-ring 75 that has (a) an outer diameter that matches the inner diameter of the Petri dish 10 and (b) an inner diameter that matches the outer diameter of the cylindrical sidewalls 30 is used, and the cylindrical sidewalls 30 are jammed into the O-ring 75 to provide an interference fit. The 35 mm m-dish made by Ibidi GmbH (ibid.com) is suitable for use as the Petri dish 10 in this embodiment.

Note that in those embodiments that use the floor of a glass Petri dish 10 to serve as the bottom panel 20, the vertical walls of the Petri dish 10 are disposed radially beyond the ceramic sidewalls 30.

The height of the ceramic sidewalls 30 may be varied to allow different amounts of media to be placed within each container as well as to accommodate possible inserts (e.g. Boyden inserts). In alternative embodiments, tall containers may be obtained by grafting a second cylinder made of a biocompatible material (e.g., glass or polycarbonate) to the top of a short ceramic cylinder. Positioning the ceramic cylinder at the bottom of the container facilitates the application of TTFields to bottom of the container where cells are plated.

Figure 2:
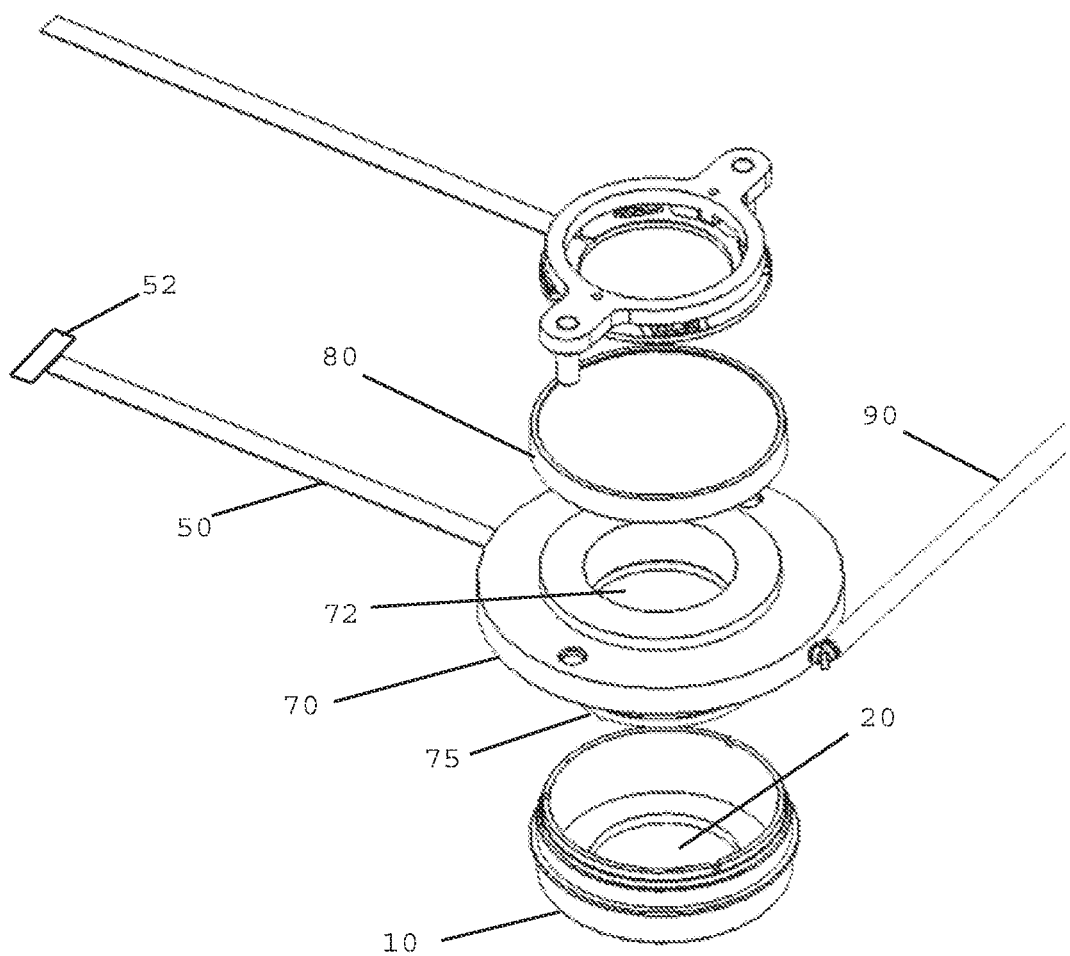
FIG. 2 is an exploded view of the FIG. 1 apparatus.
Figure 3:
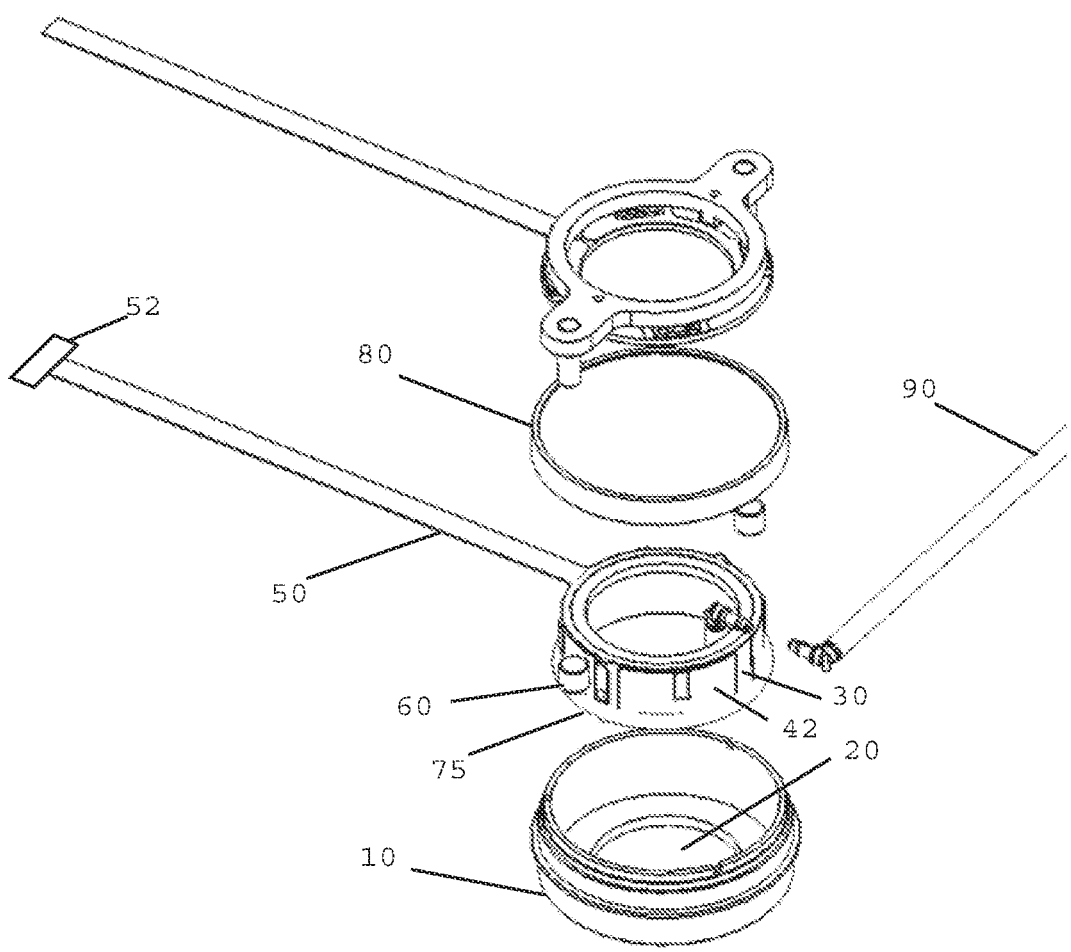
FIG. 3 depicts the FIG. 2 view with the upper housing removed in order to reveal the ceramic sidewalls.

Optionally, tubing 90 is provided to allow for media replacement without the need to remove the dish 10 from the stage of the microscope (not shown) while maintaining sterile conditions. Although only a single piece of tubing 90 is depicted in FIGS. 1-3, two or more pieces of tubing (not shown) may be used in alternative embodiments.

Figure 4:
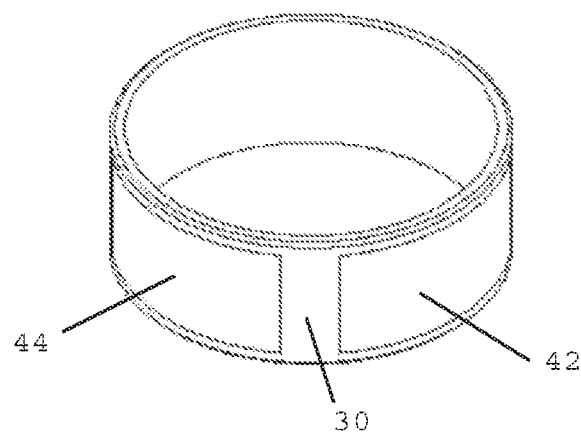
FIG. 4 depicts a perspective view of the cylindrical ceramic sidewalls of the FIG. 1 embodiment.
Figure 5:
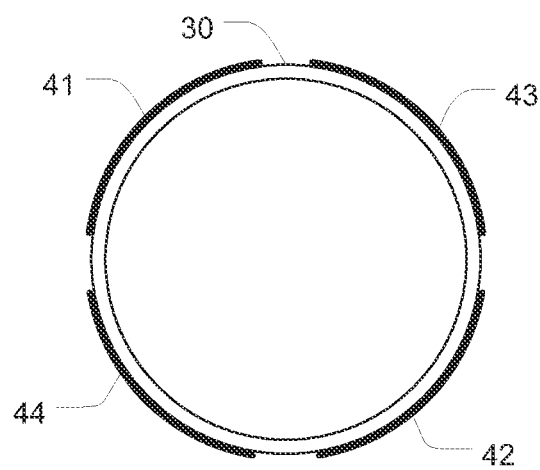
FIG. 5 depicts a schematic plan of view of the components that appear in FIG. 4.

As best seen in FIGS. 4-5, a plurality of electrodes 41-44 is disposed on the at least one outer surface of the ceramic sidewalls 30 at positions selected so that when the sample is positioned in the container, application of a voltage between the plurality of electrodes 41-44 induces an electric field through the sample. In some embodiments, at least four electrodes 41-44 are disposed on the outer surface (or surfaces) of the ceramic sidewalls 30 at positions selected so that when the sample is positioned in the container, (a) application of a voltage between a first subset of the at least four electrodes induces an electric field in a first direction through the sample, and (b) application of a voltage between a second subset of the at least four electrodes induces an electric field in a second direction through the sample. The electrodes 41-44 may be formed on the outer surface of the ceramic sidewalls 30 by painting panels of a conductive material directly onto the outer surface, by applying a thin sheet of a conductive material using a suitable conductive adhesive, by compressing a thin leaf of metal (e.g., gold) directly onto the outer surface of the ceramic sidewalls 30, or by a variety of alternative approaches that will be apparent to persons skilled in the relevant arts.

The electrodes 41-44 and the region of the ceramic sidewalls 30 beneath the electrodes 41-44 form capacitive electrodes through which the electric field is coupled into the sample (i.e. the cell culture). The advantage of using a ceramic with a high relative permittivity is that the impedance of the electrodes can be kept low whilst maintaining the walls at a thickness that ensures the mechanical rigidity of the dish-like apparatus.

In the illustrated embodiment and as best seen in FIG. 5, the sidewalls 30 are cylindrical and four electrodes 41-44 are positioned on respective quadrants of the cylindrical sidewalls 30. The first electrode 41 is disposed at a first position on the cylindrical sidewalls 30 and the second electrode 42 is disposed at a second position on the cylindrical sidewalls 30 that is opposite to the first position. The third electrode 43 is disposed at a third position on the cylindrical sidewalls 30 and the fourth electrode 44 is disposed at a fourth position on the cylindrical sidewalls 30 that is opposite to the third position.

Application of an AC voltage between a first subset of electrodes consisting of electrodes 41 and 42 induces an electric field in a first direction through the sample. Application of an AC voltage between a second subset of electrodes consisting of electrodes 43 and 44 induces an electric field in a second direction through the sample. When the electrodes are arranged as depicted in FIGS. 4-5, the second direction is perpendicular to the first direction. If one subset of electrodes (e.g. electrodes 41 and 42) is shifted by a small angle (e.g. less than 10°), the second direction will be roughly perpendicular to the first direction.

A plurality of electrical conductors 50 is provided, and each of the plurality of electrical conductors 50 provides electrical contact with a respective one of the plurality of electrodes 41-44 and routes electricity between a given one of those electrodes 41-44 and a respective corresponding electrical terminal. In embodiments that have at least four electrodes, at least four electrical conductors 50 are provided, and each of the at least four electrical conductors 50 provides electrical contact between a respective one of at least four electrical terminals and a respective one of the at least four electrodes 41-44. The conductors 50 may be implemented using individual wires, ribbon cables, flex circuits, etc. Each of the conductors 50 may be connected to the electrodes 41-44 using any appropriate approach including but not limited to soldering, electrical connectors, etc. In some embodiments, each of the electrical terminals is disposed in a single electrical connector 52 (shown in FIGS. 2 and 3).

Each of the plurality of electrodes 41-44 and each of the plurality of electrical conductors 50 is positioned with respect to the transparent region of the bottom panel 20 so as not to interfere with the optical path described above. For example, in those embodiments where the entire bottom panel 20 is transparent, each of the plurality of electrical conductors 50 may traverse a path that circumvents the entire transparent bottom panel 20. The conductors are used for applying electric fields to a sample that is positioned in the container. For example, an AC voltage between 50 and 500 kHz may be applied across the conductors that are wired to the first electrode pair 41-42 and then across the conductors that are wired to the second electrode pair 43-44 in an alternating and repeating sequence. This will cause electric fields with different directions to be generated in the samples that are located in the container in a corresponding alternating and repeating sequence. In alternative embodiments, the voltages may be applied across different combinations of the electrodes 41-44 in a different sequence to provide alternative field shapes or directions.

The dish-like apparatus described herein is useful for various assays such as: watching the evolution of cellular structures in response to TTFields; using fluorescent dyes, GFP-tagged proteins, or other labeled proteins; scanning frequencies to determine the most effective frequency; measuring cells' sensitivity assays to different TTFields intensities; measuring the diameter of cells; measuring migration rates and directions during TTFields application; determining TTFields' effect on cell invasion using a Boyden chamber inserted into the container; determining TTFields' effect intracellular on different structures/molecules within the cell; and determining TTFields' effect on cell grown in 3D structure (e.g. microspheres) using specific inserts which maintain and support the 3D structures (e.g. agarose mesh).

As best seen in FIGS. 2-3, in some embodiments, the container has a transparent cover 80 that maintains sterile conditions within the container and minimizes evaporation while allowing for gas exchange. The cover 80 is preferably made of a transparent material that allows light from the microscope condenser to reach sample (i.e., the cell culture), thereby enabling imaging of the sample using the light from the condenser. Optionally, a heating element may be provided to heat the transparent cover 80 to prevent liquid condensation from interfering with the viewing of the sample. Optionally, temperature sensors may be used to control the temperature of the cover 80.

Turning now to FIG. 3, at least one temperature sensor (e.g., thermistor 60) is preferably provided in thermal contact with the container (which, as described above, is formed from the ceramic sidewalls 30 and the bottom panel 20) to measure the temperature of the container. The thermistor or thermistors 60 are mounted at a position that does not interfere with the optical path described above. In some embodiments, the thermistor or thermistors 60 are mounted to the ceramic sidewalls 30 at a position that does not interfere with the optical path. In alternative embodiments, the thermistor or thermistors 60 are mounted to the bottom panel 20 at a position that does not interfere with the optical path. In some embodiments, the at least one thermistor 60 comprises two thermistors that are mounted on opposite sides of the ceramic sidewalls 30. The thermistors may be connected to ceramic sidewalls 30 using a heat conductive adhesive. The electrical wiring to the thermistors 60 (not shown) should not interfere with the optical path. In alternative embodiments, different types of temperature sensors may be used in place of thermistors.

When applying TTFields to cell cultures, Ohmic losses in the cell culture heat the cell culture medium. The thermistor or thermistors 60 are used to monitor the temperature in the container. The electric field intensity and/or the ambient temperature can then be controlled to maintain the desired temperature in the cell culture.

One example of a temperature control algorithm that is suitable for use when applying TTFields is provided below. The data from the thermistors attached to the ceramic sidewalls 30 is transferred to a processor (not shown). The processor compares the current temperature of the hottest thermistor with the temperature recorded in the previous 20 measurements and provides a prediction regarding the temperature to be reached within the next 20 measurements in the current settings. The predication is based on the following equations:

$$D = [(T_{(n)} - T_{(n-20)})] \quad \text{Equation 1}$$

$$T_{(n+20)} = T_n + D \quad \text{Equation 2}$$

Where:
D—temperature change in the last 20 measurements
$T_n$—Last temperature measured
$T_{(n+20)}$—Predicted temperature within the next 20 measurements Based upon the predicted temperature the algorithm determines the change in the electric fields intensity by changing the output currents, thus allowing for the temperature within the dish-like apparatus to reach the target temperature $T_{TARGET}$ with minimal overshooting. The degree of change in the output current is based upon the following scheme:

1. If $(T_{TARGET} - 0.4) < T_{(n+20)} < T_{TARGET}$ → don't change current
2. If $T_n < (T_{TARGET} - 0.4)$ and $D > 0.3$ → don't change current
3. If $T_n < (T_{TARGET} - 0.4)$ and $D * 20 > 0.8$ → don't change current
4. If 1-3 are false, change current as follows:
    If cooling if needed → Reduce the current by $(T_{(n+20)} - T_{TARGET}) * K_1$, but not more than $K_2$.
    If heating is needed → Increase the current by $(T_{TARGET} - T_{(n+20)}) * K_3$, but not more than $K_4$.

Where:
$T_{TARGET}$ is the target temperature
$K_1$—a constant describing the current step down
$K_2$—a constant describing the current maximal step down
$K_3$—a constant describing the current step up
$K_4$—a constant describing the current maximal step up This algorithm takes into account the differences between the temperature of the ceramic sidewalls 30 and the ambient temperature and provides accurate estimation of the temperature within the container (e.g., ±1° C.). The precise estimation of the temperature within the container is based upon extensive temperature measurements performed using the thermistors attached to the ceramic sidewalls 30. Optionally, temperature probes inserted into the media within the container may be used to supplement the temperature measurements obtained using the thermistors.

The algorithm also ensures that the temperature increase within the container from room temperature to the target temperature will take at least 25 minutes to follow the temperature rate increase in control dishes when transferred from room temperature to an incubator set to the target temperature.

In some preferred embodiments, temperature measurements are made every 1-5 seconds (e.g., every 3 seconds); the prediction algorithm starts every 2-10 seconds (e.g., every 6 seconds), and the values of the constants $K_1$-$K_4$ are as follows:
$K_1$ is between 1 and 5 mA (e.g., 2 mA or 2.2 mA)
$K_2 = 4 \times K_1$
$K_3 = K_1$
$K_4 = 2 \times K_3$ In some preferred embodiments the maximum measured load current is 546 mA; the maximum measured output voltage is 210 V; and the algorithm works with the digital trimmer steps, with a minimal current of 25 steps (e.g., corresponding to 54.6 mA) and a maximum current of 250 steps (e.g., corresponding to 546 mA).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:
1. An apparatus for optically observing a sample while applying electric fields to the sample, the apparatus comprising:
   a fluid-tight container shaped and dimensioned for holding the sample, the container having a transparent bottom panel and ceramic sidewalls affixed to the transparent bottom panel, wherein the ceramic sidewalls have at least one outer surface;

a first electrode disposed at a first position on the at least one outer surface of the ceramic sidewalls;

a second electrode disposed at a second position on the at least one outer surface of the ceramic sidewalls, wherein the second position is opposite to the first position, so that application of an AC voltage between the first electrode and the second electrode induces an AC electric field through the sample in a first direction;

a third electrode disposed at a third position on the at least one outer surface of the ceramic sidewalls;

a fourth electrode disposed at a fourth position on the at least one outer surface of the ceramic sidewalls, wherein the fourth position is opposite to the third position, so that application of an AC voltage between the third electrode and the fourth electrode induces an AC electric field through the sample in a second direction;

a first electrical conductor arranged to route electricity between a first electrical terminal and the first electrode along a path that circumvents the transparent bottom panel;

a second electrical conductor arranged to route electricity between a second electrical terminal and the second electrode along a path that circumvents the transparent bottom panel;

a third electrical conductor arranged to route electricity between a third electrical terminal and the third electrode along a path that circumvents the transparent bottom panel; and a fourth electrical conductor arranged to route electricity between a fourth electrical terminal and the fourth electrode along a path that circumvents the transparent bottom panel.

2. The apparatus of claim 1, wherein the first electrical terminal, the second electrical terminal, the third electrical terminal, and the fourth electrical terminal are all disposed in a single electrical connector.

3. The apparatus of claim 1, wherein the ceramic sidewalls are cylindrical.

4. The apparatus of claim 1, further comprising at least one thermistor mounted to the ceramic sidewalls.

5. The apparatus of claim 1, wherein the ceramic sidewalls are mounted to the bottom panel using an adhesive.

6. The apparatus of claim 1, wherein the container has an O-ring disposed between the ceramic sidewalls and the bottom panel, and wherein the ceramic sidewalls are mounted to the bottom panel using a screw mount configured to squeeze the ceramic sidewalls and the bottom panel together.

7. The apparatus of claim 1, wherein the ceramic sidewalls are cylindrical and have an outer diameter,
    wherein the ceramic sidewalls are mounted to the bottom panel using an O-ring that has (a) an outer diameter that matches the inner diameter of a Petri dish and (b) an inner diameter that matches the outer diameter of the ceramic sidewalls, and
    wherein the ceramic sidewalls are jammed into the O-ring to provide an interference fit.

8. The apparatus of claim 1, wherein the second direction is roughly perpendicular to the first direction.

* * * * *